United States Patent [19]

Mascellani et al.

[11] Patent Number: 5,547,944
[45] Date of Patent: Aug. 20, 1996

[54] DERMATAN SULPHATE POSSESSING A THROMBOLYTIC ACTIVITY, AND PHARMACEUTICAL FORMS CONTAINING IT

[75] Inventors: Giuseppe Mascellani; Pietro Bianchini, both of Corlo Di Formigine, Italy

[73] Assignee: Opocrin S.p.A., Corlo Di Formigine, Italy

[21] Appl. No.: 199,229

[22] PCT Filed: Aug. 6, 1992

[86] PCT No.: PCT/EP92/01790

§ 371 Date: Feb. 23, 1994

§ 102(e) Date: Feb. 23, 1994

[87] PCT Pub. No.: WO93/05074

PCT Pub. Date: Mar. 18, 1993

[30] Foreign Application Priority Data

Aug. 28, 1991 [IT] Italy .................... MI91A2310

[51] Int. Cl.$^6$ .................... A61K 31/725
[52] U.S. Cl. .................... 514/54; 514/62; 536/53; 536/54; 536/55.1; 536/55.2; 536/55.3
[58] Field of Search .................... 514/54, 62; 536/53, 536/54, 55.1, 55.2, 55.3

[56] References Cited

U.S. PATENT DOCUMENTS

| | | | |
|---|---|---|---|
| 4,870,166 | 9/1989 | Del Bono et al. | 536/21 |
| 4,973,580 | 11/1990 | Mascellani et al. | 514/54 |
| 5,013,724 | 5/1991 | Petitou et al. | 514/54 |
| 5,116,963 | 5/1992 | Del Bono et al. | 536/21 |

FOREIGN PATENT DOCUMENTS

91/15217   10/1991   WIPO .

OTHER PUBLICATIONS

Jaseja, et al, Canada Journal of Chemistry, vol. 67, pp. 1149–1456 (1989).
Rej et al, Carbohydrate Research, 200 pp. 437–447 (1990).
Mascellani, et al to be published in the Journal of Carbohydrate Chemistry.
Desnoyers et al. *Path. Biol.* 1989, 37(6), 759–767.
Maimone et al. *J. Biol. Chem.* 1990, 265 (30), 18263–18271.
Tollefsen et al. *J. Biol. Chem.* 1986, 261 (19), 8854–8858.
Maaroufi et al. *Thromb. Res.* 1990, 59, 749–758.
Dol et al. *Thromb. Res.* 198, 52, 153–164.
Linhardt et al. *Biochem. Pharmacol.* 1991, 42(8), 1609–1619.
Volpi et al. *Il Faramco* 1992, 47 (Suppl. 5), 841–853.

Primary Examiner—Gary L. Kunz
Assistant Examiner—Kathleen Kahler Fonda
Attorney, Agent, or Firm—Bucknam and Archer

[57] ABSTRACT

A natural dermatan sulphate with antithrombinic activity in excess of 220 U/mg which comprises an oligosaccharide sequence with a high degree of sulfation, having formula (III)

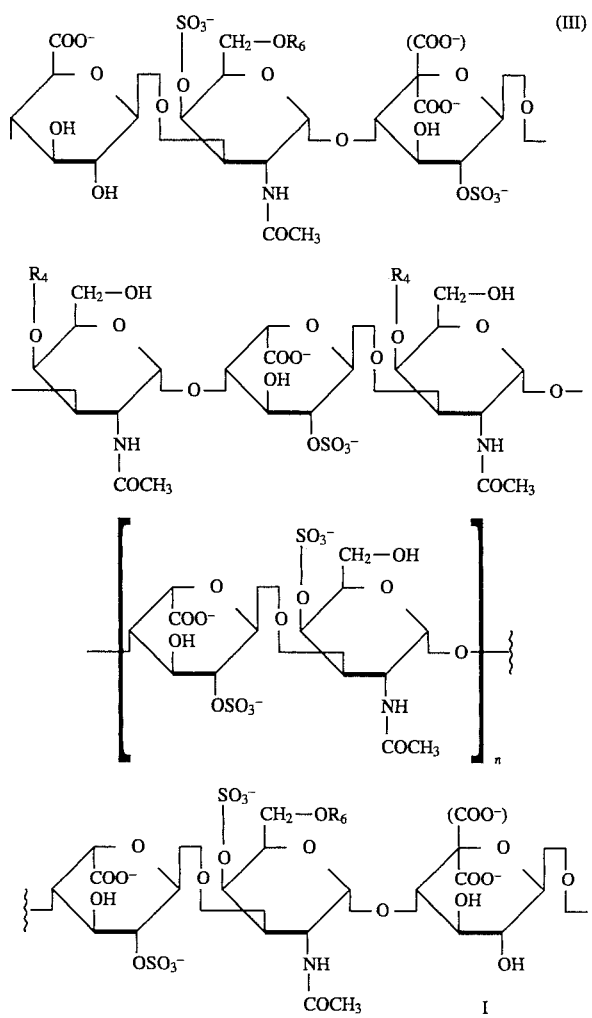

in which: n=integers 1 or 2; $R_4=SO_3$, or H; $R_6=H$, or $SO_3$; G=glucuronic acid: I—non-sulfated uronic acid, preferably glucuronic acid, is extracted from organs, and subsequently purified in mild operating conditions, at pH 5-7, isolation and fractionation being carried out with macroreticular ion exchange resins, having a particle size of less than 10 μ.

14 Claims, 4 Drawing Sheets

DERMATAN SULPHATE POSSESSING A THROMBOLYTIC ACTIVITY, AND PHARMACEUTICAL FORMS CONTAINING IT

This is the U.S. national phase of PCT/EP92/01790, filed Aug. 6, 1992.

Dermatan sulphate is a hexosaminoglycan of the heparin family. It is only recently that it has been looked upon as one of the physiological constituents of the vascular wall, and from this standpoint its anti-thrombogenic property has been examined (Desnoyers P. et al.; Pathologie Biologic, June 1989, 759).

Patent applications claiming the extraction process and utilisation as a thrombosis prevention drug have also been filed. European Patent 199,033 described a process of extraction from aorta and myocardium or other vascularised tissues, such process including micronisation of the tissue, dissociation of the proteoglycan with urea, precipitation and fractionation. The product is claimed as a preventive antthrombotic agent as it possesses activated antifactor ten activity, (AXa), it induces a lowering of the antithrombin III (ATIII) plasma levels and possesses little or no fibrinslyric activity.

EP 238,994 claims a dermarsh sulphate extracted by means of proteolysis, precipitation as a quaternary ammonium salt (cetyl-dimethylethyl ammonium and similar), and purification of the product through formation of a calcium salt in an alkaline medium. The product is characterised as a polysaccharide consisting of the repetitive unit (II)

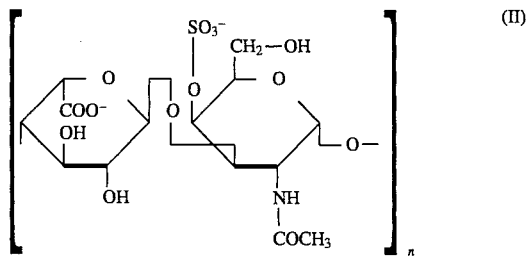

One subject of this invention consists of a reasonably mild process such that it will preserve the chemical structure of dermatan, in particular preventing or restricting desulphation thereof, and specific process so that it will select a dermatan sulphate characterised by an oligosaccharide sequence including at least eight monosaccharides with a high degree of sulphation. This sequence, responsible for interaction with heparin colactor II (HClI), has the minimum structure shown in (III)

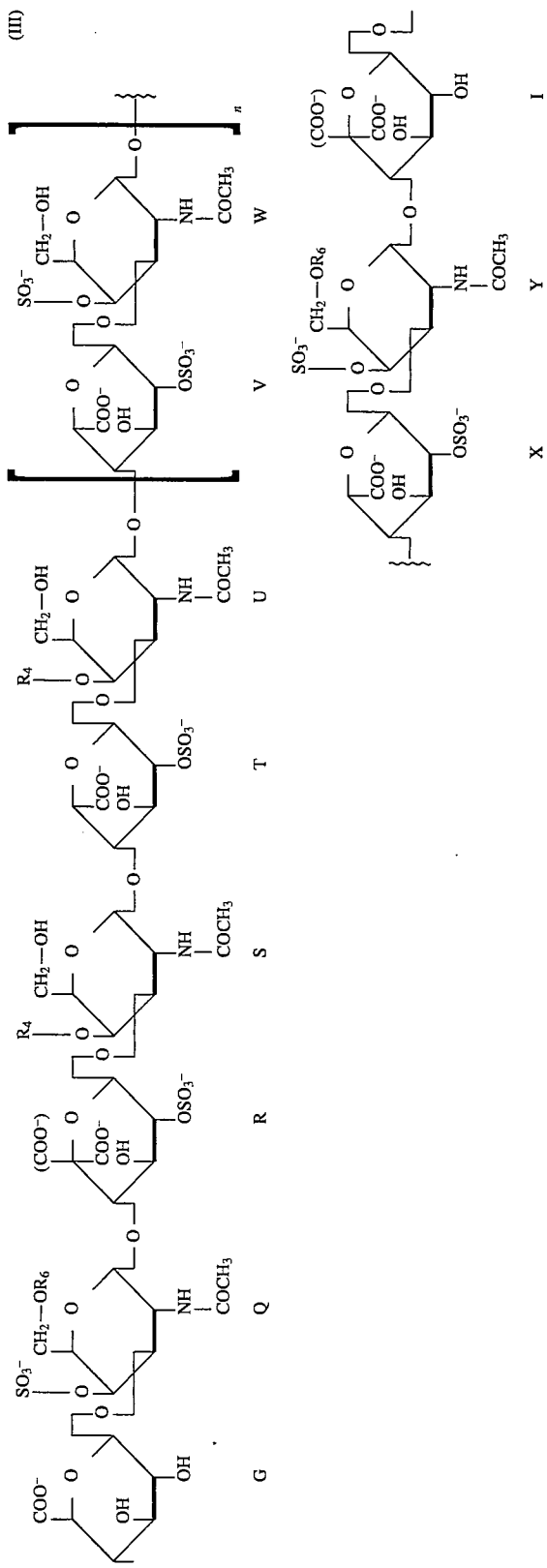

in which:

G=glucuronic acid;

n=integers 1 or 2;

I=non-sulphated uronic acid, preferably glucuronic acid;

$R_4=SO_3^-$ or H;

$R_6=H$ or $SO_3^-$;

and consists of at least 4 or 5 disulphated disaccharides formed by N-acetyl galactosamine-4-sulphate (Gal-NAc-$4SO_3^-$)-uronic acid-2-sulphate (Ido-$2SO_3^-$).

A hexasaccharide sequence with high affinity for HCII, consisting of three disulphated disaccharides of formula (IV) was identified in dermatan sulphate (Maimone M. M., Tollefsen D. M., J. Biol. Chem. 265, 30, 18263–18271 (1990));

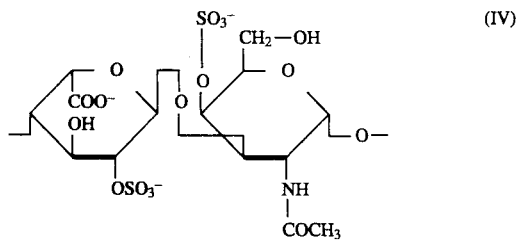

(IV)

The subject of the invention is therefore also a dermatan sulphate in whose structure there is a sequence containing a number of disulphated disaccharides in excess of three. It was found surprisingly that sequences consisting of a higher number of disulphated disaccharides (IV), hitherto never described, are contained in dermatan sulphate and are responsible for greater activity, contrary to what was stated by Maimone and Tollefsen, according to whom the hexasaccharide constitutes the sequence with the highest affinity for and activity in respect of HCII. The sequences of the present invention are included among two glucuronic acids having a structure (V). Glucuronic acid is an epimer on carbon C-5 of iduronic acid (VI).

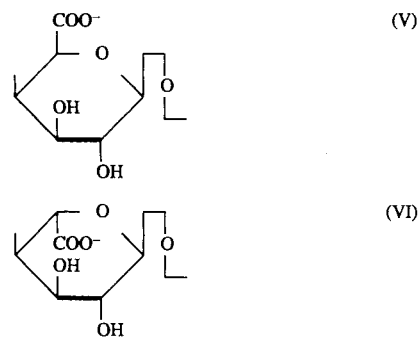

Figure 1:
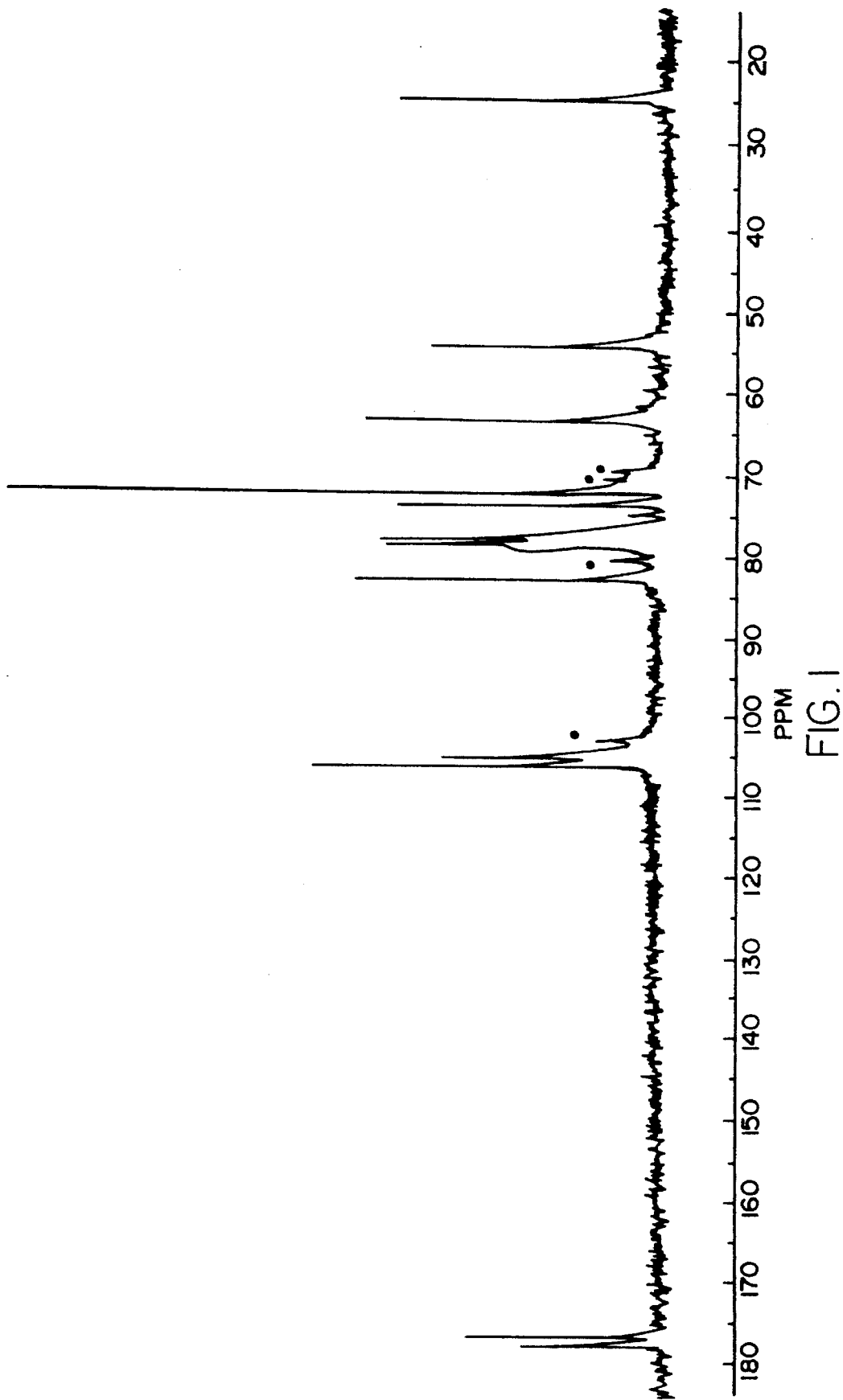
FIG. 1 shows the $^{13}$CNMR spectrum of the dermatan sulfate according to formula III.

Surprisingly, through minor signals of non-destructive $^{13}$C-NHR spectral analysis it is possible to identify the intact and peculiar sequence responsible for the activity in the dermatan sulphate chain obtained according to the invention (see FIG. 1).

The dermatan sulphate of the present invention has thrombolytic activity, in other words it is capable not only of inhibiting venous thrombus formation but especially of favouring thrombus dissolution at surprisingly low doses, in the region of 0.2–1 mg/kg according to experimental models, and with a long-lasting action. Dermatan sulphate produced according to the invention inhibits thrombin through activation of a plasma inhibitor known as Heparin Co-Factor II (HCII), while it does not act on antithrombin III (ATIII), activated selectively by heparin or more precisely by a specific sequence contained in about 30% of heparin molecules.

The dermatan sulphate of the present invention is practically inactive in vitro on various parameters relating to blood coagulation (APTT, AXa, Heptest), but nevertheless inhibits thrombin both through HCII and by inhibition of thrombin generation itself. On HCII, dermatan sulphate produced according to the present invention is surprisingly more active than the WHO fourth heparin standard.

In vitro, DS (which abbreviation from now on refers to dermatan sulphate obtained according to the invention) inhibits platelet aggregation induced by epinephrine, arachidonic acid, thrombin, collagen and ADP. It inhibits platelet aggregation induced by fMLP-activated granulocytes at doses comparable with that of heparin, but is much more active than the latter in inhibiting platelet calcium movement. In vivo, in experimental thrombosis induced by ligature of the vena cava in the rat (in line with the model suggested by Reyers S. et al., Thromb. Res. 18, 699 (1980)), DS administered intravenously has an $ED_{50}$ of 0.65 mg/kg, administered subcutaneously and evaluated 2 hours after ligature it has an $ED_{50}$ of 8.24 mg/kg, and of 10.3 mg/kg evaluated 6 hours after ligature of the vein. If administered by intravenous route after the thrombus has already formed, DS at 2.5 mg/kg is found to reduce the thrombus weight to the same extent as 2500 U/kg of urokinase, when the effect is evaluated 10 hours after treatment. The DS and urokinase dose-effect curves, even evaluated six hours after treatment, coincide in the ratio of 1 mg/1000 U. Zn intravenous infusion tests 1 mg/kg of DS appears more active than 1000 U/kg of urokinase. DS administered intravenously is active at a dose of 0.1 mg/kg in inhibiting 90% of a Jugular vein thrombosis induced by Protein Complex Concentrate (PCC) in the rabbit, and in inhibiting 70% of a thrombosis induced by a PCC/RVV (Russel Viper Venom) combination; (Fareed J. et al.; Sem. Thromb. Haemost. 11, 155–157 (1985)).

DS administered intravenously in a mesenteric, arteriolar or venular model (in line with Hladovec's model, J. Physiol. Bohemoslavaca 25, 551–54 (1975)) has an $ED_{50}$ of 0.4 mg/kg, and when administered subcutaneously of 2.6 mg/kg. Arterial (platelet) thrombosis is inhibited by intravenous DS administration with an $ED_{50}$ of 1.95 mg/kg (in the platinum wire model). DS shows very little effect on bleeding time.

Figure 2:
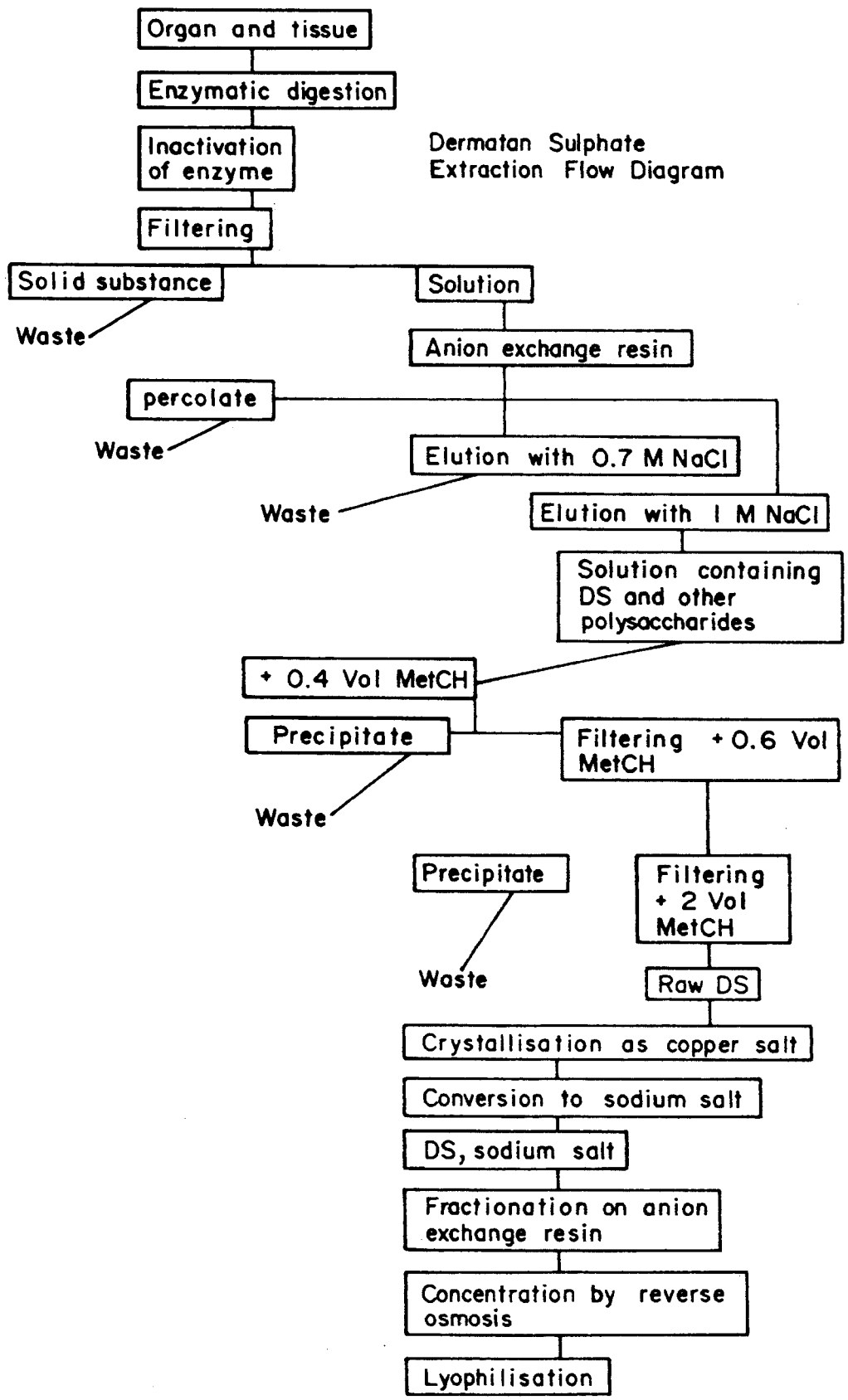
FIG. 2 is a flow sheet illustrating the process of preparation of the dermatan sulfate according to formula III.

Dermatan sulphate obtained according to the present invention is extracted from organs and tissues by a process which taken as a whole, as already stated, is also a subject of the present invention. This process, set out diagrammatically in the flow sheet in FIG. 2, is characterised by the fact that:

a) the animal organs are adequately ground and then treated with proteolytic enzymes, operating at a pH lying between 5 and 7, such as for example papain;

b) digestion is carried out hot at a temperature lying between 60° and 90° C., and is monitored by analysis of the amino acids released; digestion is stopped on average after 4–6 hours, as soon as the quantity of aminic nitrogen in solution remains constant;

c) the reaction mass is inactivated by heating at 80° C. for 15';

d) the product is filtered and the solid material discarded;

e) the solution containing the polysaccharides is percolated over a strong anion exchange macroporous resin column in Cl⁻ form, of the types known in the trade as DOWEX MSAI, Duolite A161, Amberlite IRA900, IRA904, Levatite MP5080, Lewatit MP 500 A, etc. The weight/volume ratio between the weight of the raw polysaccharides (in g) and the volume (ml) of the resin bed must be $\geq 100$. The polysaccharides remain fixed on the resin;

f) the resin is eluted with 0.3–0.7M sodium chloride solution. Polluting substances such as proteins, nucleic acids, low density charge polysaccharides are removed and discarded;

g) the dermatan sulphate is eluted from the resin with sodium chloride solution at molarity $\geq 1$;

h) the solution containing dermatan sulphate is fractionareal with 0.6 volumes of solvents miscible with water, such as alcohols having up to 3 carbon atoms, or acetone. The precipitate is discarded. The filtered solution is treated with two volumes of the same solvent;

i) the precipitate formed by raw dermatan sulphate is purified as copper (or iron or calcium) salt through selective precipitation with alcohols;

l) the copper (or iron or calcium) salt is converted to dersatan sulphate sodium salt by means of a cationic exchange resin;

m) the enriched dermatan sulphate in the minimum sequence QRSTUVWXY of formula (III) is obtained by further fractionation over strong anionic exchange resin consisting of styrene-divinylbenzene copolymers functionalised with quaternary ammonium salts having about 2–8% of cross-linkage and micronised so as to have an average size of 5–8 μ, and in any case less than 10 μ.

Surprisingly this resin particle size allows separation by intramolecular charge density; this means that it selectively retains and enriches only those dersatan sulphate chains containing the minimum high density sequence of sulphate groups indicated in (III).

The product obtained is characterised by the $^{13}$C-NMR spectrum in FIG. 1, recorded in 10% D$_2$O solution on a Bruker Ac 300 instrument operating at 75.47 MHz. The chemical shifts were measured with reference to methanol as an internal standard at 51.75 ppm in relation to external TMS. The spectrum is characterised by asterisked minor signals that can be reliably assigned: in particular δ102 (C-1 of Ido-2-SO$_3^-$), δ80 (C-2 of Ido-2-SO$_3^-$), δ74 (C-4 of Ido-2-SO$_3^-$), δ69.5 (C-3 of Ido-2-SO$_3^-$), δ68.6 (C-5 of Ido-2-SO$_3^-$). These signals are characteristic of the oligosaccharide sequence containing disulphated disaccharide (IV).

EXAMPLE 1 a. Preparation and characterisation of DS according to the invention

Grind up 65 kg of bovine intestinal mucosa and place in reactor with 75 liters of water. Heat to 60° C. and add 430 g of sodium chloride and 150 g of papain 1:350 (Merck). Correct pB to 6.3 with sodium acetate. Keep the mass stirring for 4 h at 60° C. After 3.5 hours there is already no further development of free amino acids in the proteolytic process. Heat the mass to 78° C. for 10' and then filter through a filter-press on a filtering auxiliary (dicalite). 120 liters of liltrate are obtained. Percolate the solution at 45° C. in a chromatographic column 10×80 cm containing Lewatite MP 5080 in Cl⁻ form. Remove the percolate. Wash the resin with 12 liters of 0.6M NaCl solution, then sluts with 18 liters of 1.8M NaCl solution, with a flow rate of 2.5 BV/h (Bed Volume/h). Collect the solution and concentrate to 5 liters and to 1M NaCl through reverse osmosis. Add 0.6 volumes of ethanol to the solution. Leave to stand for 10 hours at SeC. Filter. To the filtrate add another 7 liters of ethanol. A precipitate of raw dermatan sulphate is obtained; collect by filtering. Redissolve the solid in 1.5 liters of water brought to 0.5M with copper acetate. To this solution add 100 g of dihydrated cupric chloride and 3 liters of ethanol. On standing, a precipitate is formed, which is collected by filtering, washed for a long time with ethanol, redissolved in 0.5 l of water acidified to pH 5.5 with acetic acid, and passed over a chromatographic column 4–25 cm containing Chelex 100 (BioRad) in H⁺ form. The solution obtained from the column is salified with NaOH to pH 6.2 and lyophilised. 39.6 g of pure dermatan sulphate are obtained. The following analyses are performed on the dermatan sulphate:

molecular weight (MW, by HPL,C over Protein Pack 125–300 columns, mobile phase 0.125M Na$_2$SO$_4$ and 2 mM NaH$_2$PO$_4$ st pH 6, on $3^{rd}$ degree polynomial calibration curve obtained with molecular weight standards);

sulphur percentage, uronic acids percentage, SO$_3^-$/COO$^-$ (by potentiometric method according to Mascellani et al., Il Farmaco Ed. Pr. 43, 165 (1988));

disaccharide composition according to Yoshida et al. (Anal. Biochem. 177, 327 (1989));

$^{13}$C-NMR;

in vitro activity on HCXI evaluated by chromogenic method and with Stachrom D. S. kit (Diagnostica Stago containing CBS 34.47 substrate) according to Dupoury et al., Thromb. Haemost., 60, 2, 236 (1988)) against WHO's heparin 4th Standard at 193.4 IU/mg;

in vivo antithrombotic activity evaluated in the vena cava ligature model in the rat, according to Rayers et al., Thromb. Res. 18, 699 (1980).

The DS obtained has the following characteristics: MWp 25,600 d (MWw=28,500, MWn=23,600, D=1.21); sulphur 5.94; uronic acids 33%; SO$_3^-$/COO$^-$=1.09; $[\alpha]^{20}_D$=−60°; disaccharide composition:

ΔDiOS=0.9%; ΔDi6S=2.7%; ΔDi4S=84.7%;

ΔDi-2,6dis=0.3%; ΔDi-2,4dis=9.2%;

ΔDi-4,6dis=2.0%; activity on heparin co-factor II a-HCII=245 U/mg; ED$_{50}$=1.02 mg/kg i.v. The DS has the $^{13}$C-NMR spectrum in FIG. 1.

b. Fractionation

Into a preparative HPLC system—Prep Jobin Yvon Model complete with injector, pump, and column 80×600 m, charge 30 g of dermatan sulphate obtained according to a) in 0.1M sodium chloride solution, in a column containing Aminex A29 (147–6602 BioRad). Carry out elutions, each time using 3000 ml of NaCl solutions with increasing molarity, at flow rates ranging from 250 to 310 ml/minute. Collect fractions of 3000 ml, concentrate to ⅕ of volume, desalify by reverse osmosis and lyophilise. The fractions obtained are shown in Table I.

Molecular weights and disaccharide composition were determined on the products obtained, with HPLC analysis of the disaccharides obtained by enzymatic demolition with chondroitinase ABC (E.C. 4.2.2.4.) according to the method suggested by Yoshida K. et al. (Anal. Biochem. 177, 327 (1988)). The anti-factor II activity mediated by the heparin co-factor II (HCII) was carried out by the chromogenie method with Stachrom D. S. kit (confining CBS 34.47 substrate—Diagnostica Stago, Asnières sur Seine, France) (Dupouy D., Sie P., Boneu B. Thromb. Haemostas. 1988, 2, 236 ). The activity is recorded in U/rag calculated on a calibration curve obtained with the 4th WHO heparin international standard of 193.4 IU/mg. The curves obtained were found to be parallel.

From Table I it emerges that the dermatan sulphate fractions eluted at a molarity equal to or greater than 0.75M have activity on HCII progressively higher than 230 U/rag and have saccharide sequences comprising 4, 5 or 7 disulphated disaccharides.

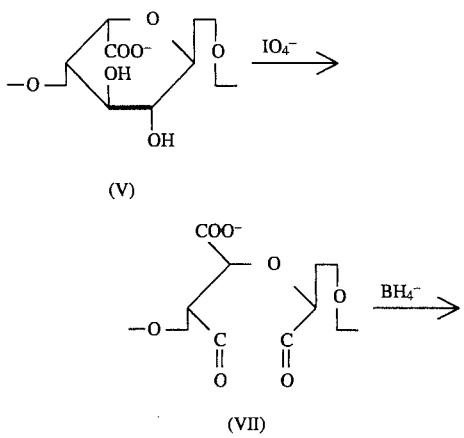

TABLE I

| Dermatan sulphate fractionated on strong anion exchange column with particle sizes of 8–10 μm. (From Example 1b). | | | | | | | | | | | |
|---|---|---|---|---|---|---|---|---|---|---|---|
| Mol. $M^{50}$ | Yield % | MW kd | HCII U/mg | Δ Di** | | | | | | | |
| | | | | -OS | -6S | -4S | -2,6diS | -2,4diS | -4,6diS | -Tris | No.* | $ED_{50}$ |
| 0.1 | 7 | 24.9 | 150 | | | | | | | | | |
| 0.25 | 1 | 25.6 | 147.5 | 1.2 | 2.3 | 87.9 | 0.6 | 6.7 | 1.2 | 0 | ~3.3 | |
| 0.5 | 1 | 26.4 | 158.9 | 1.4 | 2.3 | 87.8 | 0.6 | 6.7 | 1.3 | 0 | ~3.4 | |
| 0.75 | 68 | 26.4 | 232.8 ± 5.4 | 1.3 | 2.4 | 87.2 | 0.3 | 7.8 | 1.0 | 0 | ~3.9 | |
| 1.0 | 2 | N.D. | N.D. | | | | | | | | | |
| 1.25 | 12 | 20.0 | 271.3 ± 6.3 | 0.7 | 1.7 | 85.4 | 0.6 | 10.4 | 1.2 | 0.8 | ~4.0 | 0.81 |
| 1.5 | 5.6 | 23.5 | 350.9 ± 11.8 | 0.9 | 2.7 | 82.9 | 0.5 | 10.9 | 2.8 | 1.3 | ~4.9 | 0.65 |
| 1.75 | 2 | 33.3 | 379.6 ± 31 | 1.9 | 3.2 | 76 | 1 | 11 | 8.0 | 0.3 | ~7.0 | |
| 2.0 | 1.4 | N.D. | 432.5 ± 39 | | | | | | | | | |

Notes:
*Indicates the mean number of disaccharides Δ Di-2,4diS contained in the dermatan sulphate fractions. It is estimated that the mean molecular weight of non-salified disaccharide = 524.
**Abbreviations:
Δ DiOS, 2-acetamido-2-deoxy-3-O-(4-deoxy-α-threo-hex-L-4-enopyranosyluronic acid)-D-galactose;
Δ Di6S, 2-acetamido-2-deoxy-3-O-(4-deoxy-α-threo-hex-L-acid-4-enopyranosyluronic)-6-sulpho-D-galactose;
Δ Di4S, 2-acetamido-2-deoxy-3-O-(4-deoxy-α-L-threo-hex-4-enopyranosyluronic acid)-4-O-sulpho-D-galactose;
Δ DidiS_D, (Δ Di-2,6diS), 2-acetamido-2-deoxy-3-O-(4-deoxy-2-O-sulpho-α-L-threo-hex-4-enopyranosyluronic acid)-6-O-sulpho-D-galactose;
Δ DidiS_B, (Δ Di-2,4diS), 2-acetamido-2-deoxy-3-O-(4-deoxy-2-O-sulpho-α-L-threo-hex-4-enopyranosyluronic acid)-4-O-sulpho-D-galactose;
Δ DidiS_E (Δ Di-4,6diS), 2-acetamido-2-deoxy-3-O-(4-deoxy-α-threo-hex-L-4-enopyranosyluronic acid)-4,6-bis-O-sulpho-D-galactose.
Δ Di-Tris, 2-acetamido-2-deoxy-3-O-(4-deoxy-2-O-sulpho-α-L-threo-hex-4-enopyranosyluronic acid)-4,6-bis-O-sulpho-D-galactose.

c. Demolition

A process of controlled chemical demolition is described below which process is designed to isolate only the sequences containing iduronic acid 2-sulphate (Ido-2oSO$_3^-$) from the structure of the biopolymer obtained in a). As is well known, periodic acid oxidises the $C_2$–$C_3$ bonds of non-sulphated uronic acids to aldehyde groups, which can be reduced to hydroxy-methyl groups. The semi-acetalic bonds of the uronic acids thus treated are selectively hydrolysed in an acid medium in accordance with the following diagram -continued

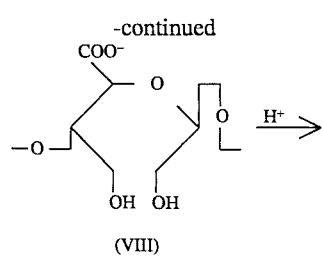

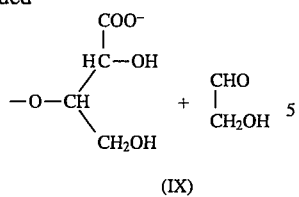

(IX)

Only the sequences containing sulphated uronic acids remain unchanged.

First stage.

Dissolve 100 g of dermatan sulphate, obtained according to a), in a liter of water, and slowly add 800 ml of a 0.5M solution of $NaIO_4$. Leave the solution stirring for 4 hours, then cool in thermostatic bath at 10° C., bring to pH 8 with N NaOH and very slowly, with stirring, add 80 g of $NaBH_4$ over the space of 4 hours. At the same time add dilute acetic acid so that the pH remains in the range 7.5–8.5. Allow to stand for one night, bring the pH to 4 with 8 N HCl in order to favour the destruction of the excess $NaBH_4$ by stirring for an hour at room temperature. Then bring the pB to 5.5 with NaOH. Precipitate the product twice with three volumes of ethanol, equal to six liters per time. After filtering and drying 80 g of oxidised and reduced dermatan sulphate (RO.DS) are obtained and are coded OP723. The RO.DS has the following characteristics: NW=15,200; sulphur 5.9%; uronic acids 32.4%; $SO_3^-/COO^-=1.1$; $[\alpha]^{20}_D=-8°$.

Second stage.

Dissolve 13.12 g of RO-DS OP723, obtained as described above, in 656 ml. of 0.1N HCl and hydrolyse for 2 hours at 60° C. Neutralise the solution to pR 6.7 with 2N NaOH. Concentrate the solution in rotavapor to 120 ml and an NaCl molarity of about 1M, then fractionise by gel-filtering over Ultrogel AcA202 (IBF) in a column 5×90 cm, at a flow rate of 2 ml/minute, Collect 20-ml fractions. Discard the dead volume. Monitor the eluents by spectrophotometer with continuous flow cell set at 205 nm. Combine the fractions from 13 to 30 (360 ml, A), from 31 to 44 (280 ml, B), from 45 to 60 (320 ml, C) and from 61 to 67 (140 ml, D).

Concentrate pool A to 55 ml and desalify over trisacryl GF O5H (IBF) in a 5×38 cm column.

Collect fractions $A_1$ and $A_2$ and lyophilise them. Concentrate pool B to 50 ml and desalify over Trisacryl GF O5M. Collect fractions $B_1$, $B_2$ and $B_3$ and lyophilise them.

Also concentrate and desalify pool C. It gives rise, after lyophilising, to fractions $C_1$, $C_2$ and $C_3$.

Table II shows the yields of the fractions obtained, the experimental molecular weights calculated by HPLC on Protein Pack 60–125 columns (Waters), the specific rotations and the experimental values of $SO_3^-/COO^-$.

TABLE II

Oligosaccharides obtained by demolition of dermatan sulphate of the present invention. Experimental values.

| | % Yield | MW | $[\alpha]^{20}_D$ | $SO_3^-/COO^-$ |
|---|---|---|---|---|
| $A_1$ | 0.2 | 3000 | nd | nd |
| $A_2$ | 3.4 | 2900 | −22.2° | 1.78 |
| $B_2$ | 3.0 | 2300 | −26.2° | 1.76 |
| $B_3$ | 3.3 | 1500 | | 1.65 |
| $C_2$ | 50 | 550 | | 1.07 |

Figure 3:
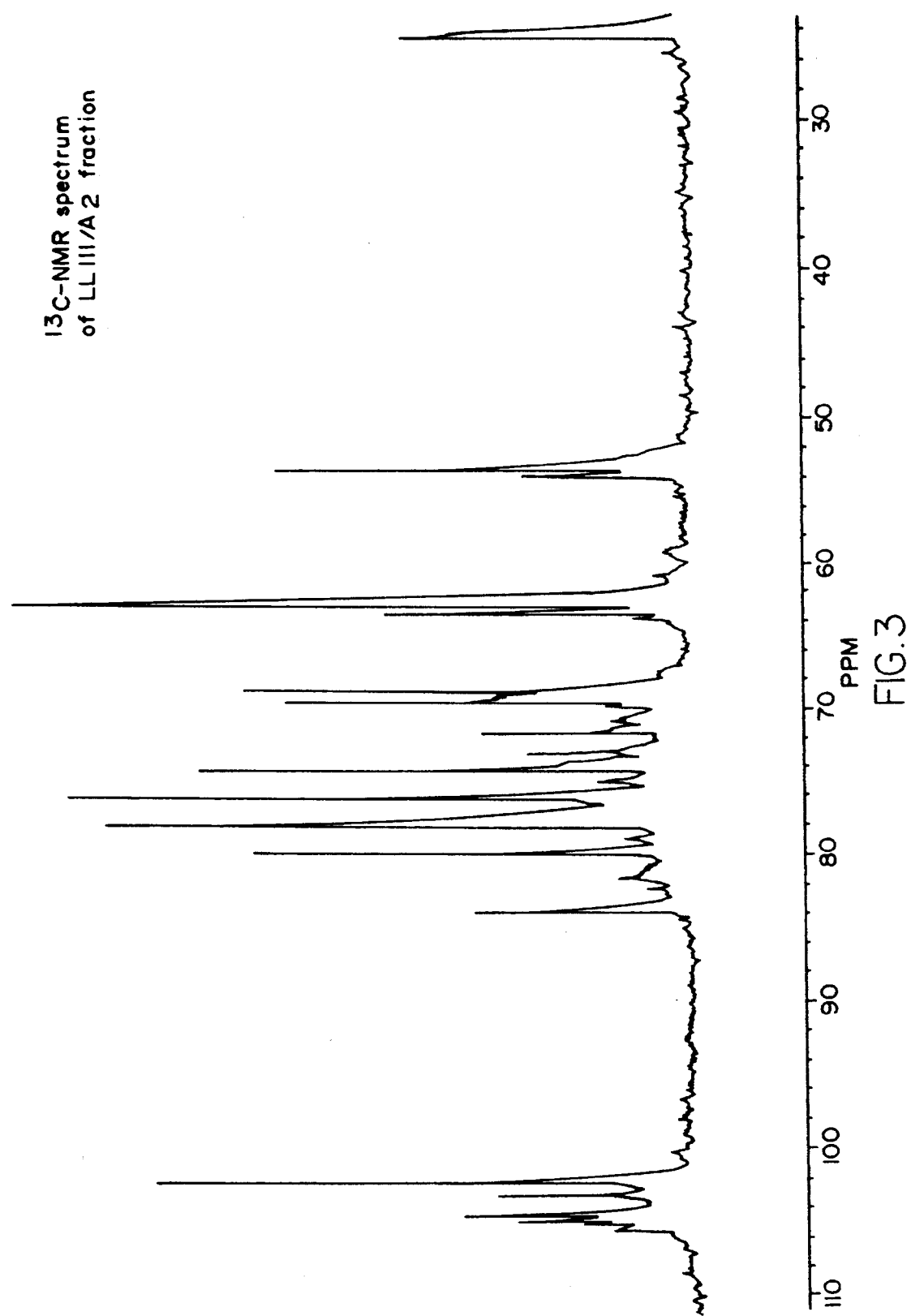
FIG. 3 and FIG. 4 show the $^{13}$CNMR spectrum of fractions $A_2$ and $B_2$ obtained by the process of demolition which is intended to isolate only the sequences containing iduronic acid 2-sulfate (Ido-$2OSO_3-$).
Figure 4:
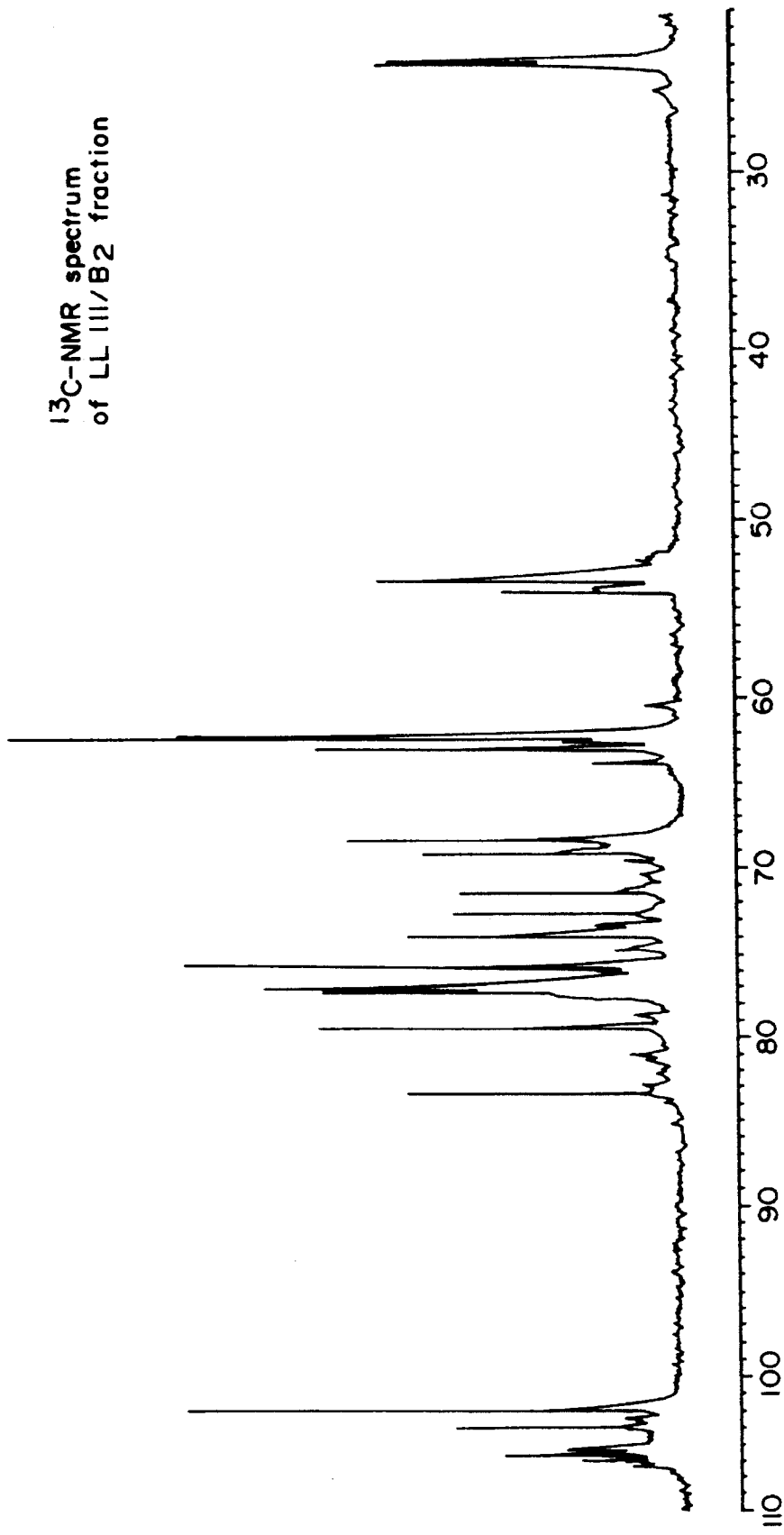

Fractions $A_2$ and $B_2$ gave the $^{13}C$-NMR spectra given in FIGS. 3 and 4 respectively. The NMR spectra and other experimental observations agree with the oligosaccharide structures indicated in formula (X) and specified in Table III.

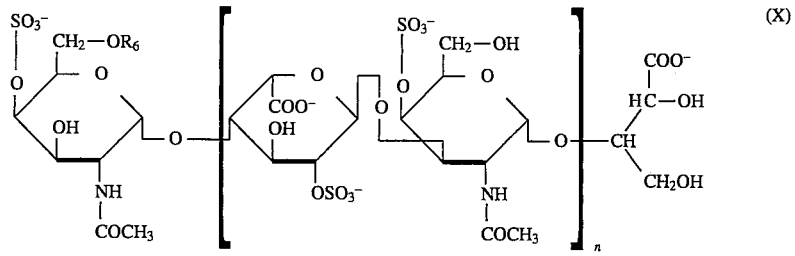

(X)

where n takes the values indicated in Table III.

TABLE III

Theoretical values of oligosaccharide sodium salts.

| | P | $R_6$ | MW | $SO_3^-/COO^-$ |
|---|---|---|---|---|
| $A_1$ | 4 | $SO_3^-$ | 2986 | 2.0 |
| $A_2$ | 4 | H | 2882.9 | 1.8 |
| $B_2$ | 3 | H | 2277.9 | 1.75 |
| $B_3$ | 2 | H | 1673 | 1.67 |
| $C_2$ | 0 | H | 462 | 1 |

The demolition process described above only for analytical purposes, in order to demonstrate the nature of the oligosaccharide sequences contained in dermatan sulphate obtained according to the invention.

The oligosaccharide structures isolated and characterised indicate that the dermatan sulphate obtained in the present invention has a structure containing the sequence GQRSTU-VWXYI, or the sequence GQRSTUXYI.

EXAMPLE 2

A dermatan sulphate is prepared according to a process similar to that described in Example 1, with the variant that the enzymatic digestion is carried out with the enzyme Alcalase (Novo) at pB 9, for eight hours at 75° C. A product having HCII activity=54 U/mg is obtained, with in-vivo $ED_{50}$ of 4.38 mg/kg (values considerably less favourable than those of the dermatan sulphate prepared according to Example 1, equal 245 U/mg and 1.02 mg/kg respectively). In the disaccharide composition only 2.4% of Δ Di-diSB is found, while in the $^{13}C$-NMR spectrum the peculiar signals of the sequence containing disulphated disaccharide at 102 ppm with reference to $C_1$ of Ido-2-$SO_3^-$ are not noted. The alkaline medium has presumably hydrolysed the $SO_3^-$ grip of the iduronic acid 2-sulphate.

EXAMPLE 3

With dermatan sulphate fractions similar to the one coded 1.25M as obtained in Example 1b) comparative studies were made on thrombolytic activity versus urokinase. Four groups of 10 rats each were anaesthetised with 1 g/kg of urethane administered in endoperitoneal physiological solution by endoperitoneal route. The vena cava of the rats was subjected to ligature in line with the Reyers test (Thromb. Res. 18, 699, 1980), and two hours after the ligature 5 mg/kg/i.v. of DS and 5000 U/kg of Ukidan (Urokinase-Serono) were administered. After eight hours the thrombus formations in the occluded vein were removed. The weights of the thrombus formations are given in Table IV.

TABLE IV

|  | mean thrombus weight, mg | standard deviation | standard error |
|---|---|---|---|
| control group two hours after ligature | 4.3 | 2.2 | 0.7 |
| group treated with 5 mg/kg DS, eight hours after ligature | 1.6 | 1.6 | 0.5 |
| group treated with Urokinase, eight hours after ligature | 2.2 | 1.6 | 0.5 |
| control group eight hours after ligature | 7.6 | 3.9 | 1.2 |

In a similar experiment, in which after an initial bolus of 2.5 mg/kg a slow infusion was given for 6 hours at a rate of 1.25 mg/kg/hour of dermatan sulphate, at the end of the experiment the reduction in thrombus weight in rats treated with 2.5 mg/kg and 1.25 mg/kg/hour of dermatan sulphate was found to be 96.1%, while the reduction in thrombus weight in the rats treated with 2500 U/kg and 1250 U/kg/hour of urokinase was 70.2% relative to the untreated controls.

EXAMPLE 4

100 kg of pig skin are ground and added to 100 l of 0.5M NaCl solution. pH is adjusted to 7.0 with sodium hydroxide. 400 g of proteolytic enzyme called Maxatase® are added. Reaction mass is stirred in a reactor for 8 hours at 60° C. It is heated to 80° C. and centrifuged in a liquid-liquid separating centrifuge. Fat phase, about 35 kg, is discarded. Aqueous phase is filtered through dicalite filter aid. Filtrate is percolated on a chromatographic column (internal diameter: 10 cm, 125 cm high) containing 10 liters of Lewatite MP 500 A (Bayer), a macroporous strong anionic exchange resin activated in form of $Cl^-$. Percolate is discarded. The resin is washed with three volumes of 0.65 NaCl solution. The product is eluted from resin with two volumes of 2.0 N NaCl. The obtained solution is concentrated and desalted by inverse osmosis up to 1 molarity of NaCl. Dersatan sulphate is precipitated with two volumes of methanol, collected and dried 67.9 g of product, almost pure, is obtained. The product gives the product coded OPD 950-965 having the following characteristics: Sulphur=5.63%, uronic acids= 32.74%, $SO_3/COO^-$=1.04, $[\alpha]^{20}_D$=−65.5°, disaccharidic composition obtained by enzymatic attack and separation by HPLC:
ΔDiOS=0.6%, ΔDi6S=1.0%, ΔDi4S=90%, ΔDi2,4diS= 7.2%, ΔDi4,6diS=1.2%. $^{13}C$-NMR spectrum, besides the peculiar signals at δ177.05 (CO-$OH_3$), δ175.79 (CO-IdoAp6), δ104.52 (IdoApl), δ103.52 (GalpNAc 1), δ 81.69 (IdoAp 4), δ77.44 (GalpNAc 4), δ76.87 (GalpNAc 3), δ76.02 (GalpNAc 5), δ72.72 (IdoAp 3), δ70.98 (IdoAp 2,5), δ62.48 (GalpNAc 6), δ54.45 (GalpNAc 2), δ24.05 (CO-$CH_3$) shows the following minor signal: $I^*_1$ (δ102), $I^*_2$ (δ80), $I^*_4$ (δ74), $I^*_3$ (δ69.5), $I^*_5$ (δ68.5) corresponding to iduronic acid 2-sulphate, and also signals at δ105.3 (GlucAp 1), δ75.4 (GlucAp 3), δ74.0 (GlucAp 2), corresponding to glucuronic acid.

The product activity in vivo has resulted corresponding to $ED_{50}$=1.5 mg/kg iv in rat.

The invention also covers all the industrial applications of DS for therapeutic uses, such as compositions with thrombolytic activity indicated in the therapy of cardiovascular disease. For this purpose the invention compounds are formulated according to conventional techniques and with standard excipients, in the form of pharmaceutical compositions for parenteral, topical and oral administration. Examples of formulations suitable for parenteral administration include sterile solutions in vials. Examples of formulations suitable for oral administration include capsules, tablets and syrups, in which the active substance may also be vehicled in the state of liposomes or micelles. Examples of formulations for topical administration include ointments containing conventional excipients.

We claim:

1. A dermatan sulfate having anti-factor II activity mediated by heparin cofactor II higher than 220 U/mg and possessing thrombolytic and antithrombotic activity, having no activity on antithrombin III, containing an oligosaccharide sequence of formula

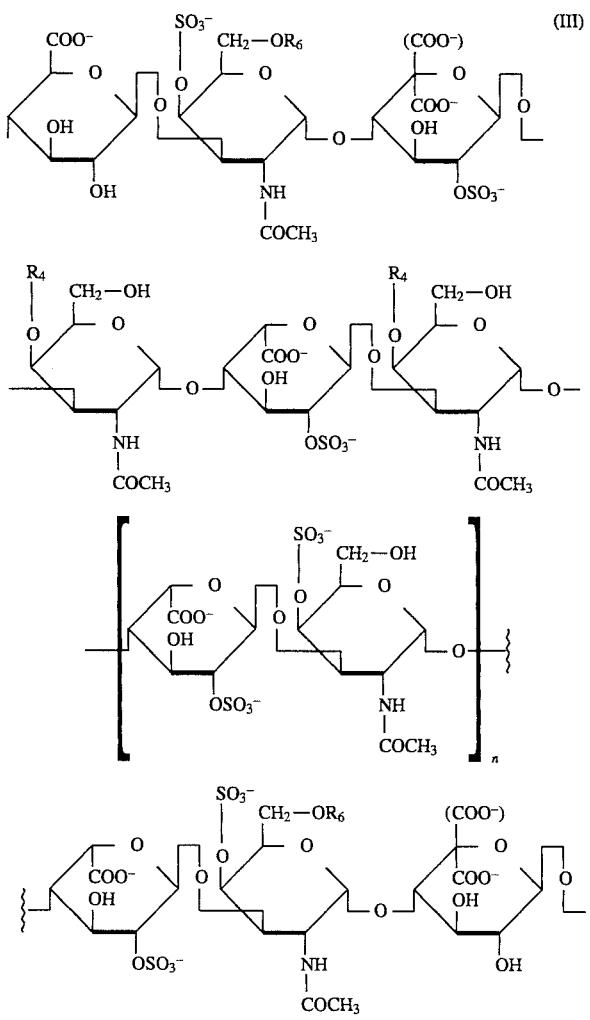

wherein n is 1 or 2; $R_4$ is $SO_3$— or H; $R_6$ is H or $SO_3$—, which comprises one glucuronic acid unit at one end and a non-sulfated uronic acid unit at the opposite end and at least four disulfated disaccharides formed by uronic acid-2-sulfate-N-acetyl galactos-amine-4-sulfate (Ido-2SO₃-Gal-NAc-4SO₃—) of formula

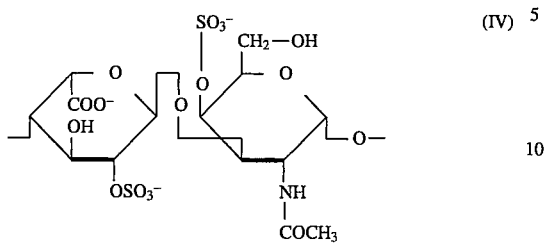

wherein the sulfate/carboxylate ratio is in the range of 1.00–1.200, which exhibits a $^{13}$C Nuclear Magnetic Resonance spectrum with a signal at 102 attributable to the C-1 of iduronic acid 2-0-sulfate; a signal at 80 attributable to the C-4 of iduronic acid 2-0-sulfate; a signal at 74 attributable to the C-2 of iduronic acid 2-sulfate; a signal at 69.5 attributable to the C-3 of iduronic acid 2-sulfate and a signal at 68.6 attributable to the C-5 of iduronic acid 2-sulfate, these signals being characteristic of said disulfated disaccharide unit (IV).

2. The dermatan sulfate according to claim 1 which inhibits venous thrombus formation and favors thrombus dissolution in a patient at a dose 0.2–1 mg/kg of body weight of the patient.

3. The dermatan sulfate according to claim 1 which has a molecular weight of 20±2.0 KDa.

4. The dermatan sulfate according to claim 1 which has a molecular weight of 25±2.5 KDa and 30±3.0 KDa.

5. The dermatan sulfate according to claim 1 which has 4 or 5 or 6 or 7 disulfated disaccharide units.

6. A process of preparing of dermatan sulfate from organs and tissues, said dermatan sulfate having anti-factor II activity mediated by heparin cofactor II higher than 220 U/mg and possessing thrombolytic and antithrombotic activity having no activity on antithrombin III containing an oligosaccharide sequence of formula

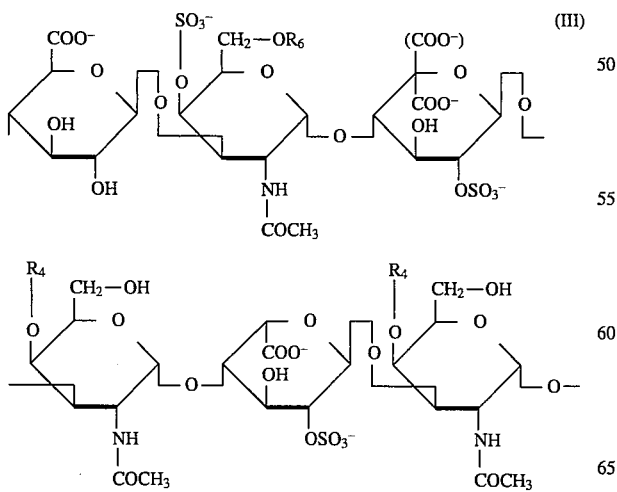

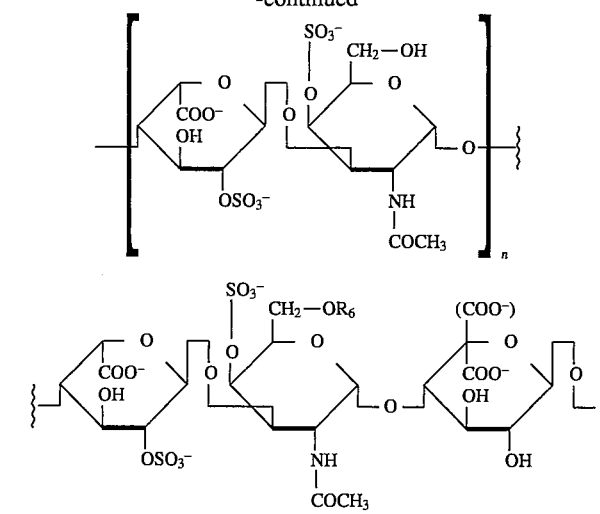

wherein n is 1 or 2; $R_4$ is $SO_3^-$ or H; $R_6$ is H or $SO_3^-$, which comprises one glucuronic acid unit at one end and a non-sulfated uronic acid unit at the opposite end and at least four disulfated disaccharides formed by uronic acid-2-sulfate [Ido-2SO₃-] -N-acetyl galactosamine-4-sulfate (Ido-2SO₃-Gal-NAc-4SO₃—) of formula

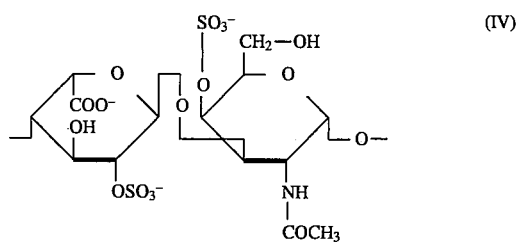

which comprises the steps of
1) grinding said organs and tissues to obtain ground material, treating the ground material with a proteolytic enzyme at a pH between 5 and 7, until the quantity of α-aminic nitrogen is constant;
2) inactivating the enzyme by heating at 80° C. to obtain a solid and a solution; filtering off the solid;
3) passing said solution from step 2) which contains dermatan sulfate over a strong anion exchange resin having particle size of 0.3–1.3 mm;
4) eluting with a neutral solution of a salt with molarity between 0.7 and 0.9M to remove proteins, nucleic acids and other impurities;
5) then eluting the resin with a sodium chloride solution of at least 1 molarity;
6) fractionating the column eluate from step 5) with a solvent miscible with water to obtain a precipitate and a solution;
7) removing the precipitate;
8) crystallizing the dermatan sulfate in the solution from step 7) as a less soluble salt of a bivalent metal which is copper, iron or calcium;
9) regenerating the dermatan sulfate from said salt obtained in step 8) as sodium salt through a cation exchange resin and eluting the resin;
10) fractionating the eluate to obtain said dermatan sulfate of formula III by anion exchange chromatography on a strongly basic resin, said resin having been functionalized with a quaternary ammonium salt, having 2–8% of cross-linkage and particle size less than or equal to 10 μ.

7. The process according to claim 6, wherein the proteolytic enzyme used is papain at pH 6-7, in the ratio of 10-20,000 U USP per kg of organs and tissues.

8. The process according to claim 6 wherein in step 3) the anion exchange resin consists of a macroreticular styrene-divinylbenzene matrix, functionalized with quaternary ammonium groups and having a particle size of 0.3-1.3 mm, equivalent to 16-50 mesh, said resin being used in a resin bed volume/polysaccharides weight ratio >100.

9. The process according to claim 6 wherein in step 4) the salt used to elute the polysaccharides from the resin is a member selected from the group consisting of NaCl, KCl, $CaCl_2$, $NANO_3$, $KNO_3$ and $Na_2SO_4$.

10. The process according to claim 6 wherein in step 5) said solvent is a member selected from the group consisting of methanol, ethanol, propanol, isopropanol, acetone and mixtures thereof.

11. The process according to claim 6 wherein said cation exchange resin in step 9) is a polymer with 8-16% of cross-linkage, functionalized with sulphonic groups, or is a chelating resin for copper and other metals, consisting of a functionalized polymer matrix with iminodiacetic groups.

12. The process according to claim 6 wherein in step 10) the resin of particle size less than 10 μ consists of a polymer matrix functionalized with quaternary ammonium groups with cross-linkage percentage between 4 and 8%, or of a silica matrix functionalized with quaternary ammonium groups.

13. A pharmaceutical composition with thrombolytic activity for the treatment of cardiovascular diseases, containing an effective amount of dermatan sulfate according to claim 1 and a pharmaceutically acceptable carrier.

14. A composition according to claim 13 for parenteral or oral or topical administration, in the form of injectable sterile solutions or suspensions, capsules, tablets, syrups, creams or ointments.

\* \* \* \* \*